(12) United States Patent
Schneider et al.

(10) Patent No.: US 7,226,904 B2
(45) Date of Patent: Jun. 5, 2007

(54) AGENTS AND METHODS FOR PROMOTING BONE GROWTH

(75) Inventors: Gary B. Schneider, Hudson, OH (US);
Steven N. Popoff, Warrington, PA (US);
Fayez Safadi, Philadelphia, PA (US)

(73) Assignees: Northeastern Ohio Universities College of Medicine, Rootstown, OH (US); Temple University, Philadelphia, PA (US)

( * ) Notice: Subject to any disclaimer, the term of this patent is extended or adjusted under 35 U.S.C. 154(b) by 34 days.

(21) Appl. No.: 11/190,665

(22) Filed: Jul. 27, 2005

(65) Prior Publication Data

US 2005/0261172 A1 Nov. 24, 2005

Related U.S. Application Data

(62) Division of application No. 10/045,673, filed on Nov. 9, 2001, now Pat. No. 7,038,010.

(60) Provisional application No. 60/247,464, filed on Nov. 9, 2000.

(51) Int. Cl.
*A61K 38/14* (2006.01)

(52) U.S. Cl. .......................................... 514/8; 530/322

(58) Field of Classification Search ...................... None
See application file for complete search history.

(56) References Cited

U.S. PATENT DOCUMENTS

| 5,641,747 A | 6/1997 | Popoff et al. | |
|---|---|---|---|
| 6,103,709 A | 8/2000 | Norman et al. | |
| 6,410,269 B1 * | 6/2002 | Yamamoto | 435/69.6 |

OTHER PUBLICATIONS

International Search Report dated Apr. 1, 2003.
"Boning up with Novel Peptides" by Schneider, BioOhio 2000, Nov. 9-10, 2000, Cleveland, Ohio.
"The Anabolic Effect of Vitamin D Binding Protein-Macrophage Activating Factor (DBP-MAF) and a Novel Small Peptide on Bone" by Schneider, et al., *Journal of Bone and Mineral Research*, Twenty-Third Annual Meeting of the American Society for Bone and Mineral Research, Phoenix, Arizona, Oct. 12-16, 2001.
Abstract—"The Effects of a Group of Novel Anabolic Peptides on Bone Density and Bone Strength in Adult Rats" by Schneider, et al., *J. Bone & Mineral Research*, 2003, Vol. 18 (Suppl. 2) p. S275.
Abstract and Poster Presentation—"The Effects of Novel Anabolic Peptides on Bone Density and Bone Strength in Adult Rats" by Schneider, et al., ASBMR 25th Annual Meeting, Sep. 19-23, 2003, Minneapolis, Minnesota.
Abstract M26—"A Novel Anabolic Peptide Activates Osteogenic Expression in Rat Stromal Cells" by Schneider, et al., The American Society for Bone and Mineral Research (ASBMR) May 24-25, 2004, Hyatt Regency Bethesda, Bethesda, Maryland.
Poster Presentation—"A Novel Anabolic Peptide Activates Osteogenic Expression in Rat Stromal Cells" by Schneider, et al., The American Society for Bone and Mineral Research (ASBMR) May 24-25, 2004, Hyatt Regency Bethesda, Bethesda, Maryland.
Abstract—"pQCT Analysis of the Anabolic Effects of a Group of Novel Small Peptides on Bone in Intact Adult Rats" by Schneider, et al., *J. Bone & Mineral Research*, 2002, vol. 17 (Suppl. 1), p. S377.
Poster Presentation—"pQCT Analysis of the Anabolic Effects of a Group of Novel Small Peptides on Bone in Intact Adult Rats" by Schneider, et al.
"Effect of Pharmaceutical Bone Growth Stimulation with Novel Anabolic Peptides: Biomechanical and Bone Density Measurements in a Rat Model" by Askew, et al, Proceedings of IMECE'03, 2003 ASME International Mechanical Engineering Congress & Exposition, Washington, D.C., Nov. 16-21, 2003.
Abstract—"The Anabolic Effect of Vitamin D Biding Protein-Macrophage Activating Factor (DBP-MAF) and a Novel Small Peptide on Bone" by Schneider, et al., *J. Bone & Mineral Research*, 2001, vol. 16 (Suppl. 1), p. S231.
Poster Presentation—"The Anabolic Effect of Vitamin D Biding Protein-Macrophage Activating Factor (DBP-MAF) and a Novel Small Peptide on Bone" by Schneider, et al.
"The Anabolic Effects of Vitamin D-Binding Protein-Macrophage Activating Factor (DBP-MAF) and a Novel Small Peptide on Bone" by Schneider, et al., *Critical Reviews in Eukaryotic Gene Expression*, 13(2-47):277-284 (2003).

* cited by examiner

*Primary Examiner*—Cecilia J. Tsang
*Assistant Examiner*—Roy Teller
(74) *Attorney, Agent, or Firm*—Calfee, Halter & Griswold LLP

(57) ABSTRACT

Agents for promoting bone deposition and growth in a mammalian subject. The agents are O-glycosylated and non-glycosylated peptides that are derived from vitamin D binding protein, collectively referred to hereinafter as "DBP" peptides. The DBP peptides are from 3 to 18, preferably from 4 to 14 amino acids in length and comprise a sequence which is at least 80% identical, preferably at least 90% identical to the amino acid sequence of a fragment contained within domain III of DBP. Methods for promoting bone deposition in a subject in need of the same are also provided. The methods comprise administering to the subject a therapeutically effective quantity of an agent selected from the group consisting of an activated form of vitamin D binding protein referred to hereinafter as "ADBP", one or more DBP peptides, and combinations thereof. The agents may be administered locally or systemically.

9 Claims, 21 Drawing Sheets

NH₂-Thr Pro Thr Glu Leu Ala Lys Leu Val Asn Lys Arg Ser Glu-COOH
　　　　　　　|
　　　　　　　O
　　　　　　　|
　　　α-D-N-Acetylgalactosamine

FIGURE 1

NGP = nonglycosylated peptide

Goldner Trichrome Stain of Femur from Local Peptide Injection

AGENTS AND METHODS FOR PROMOTING BONE GROWTH

CROSS-REFERENCE TO RELATED APPLICATIONS

This divisional application claims priority to U.S. application Ser. No. 10/045,673, filed Nov. 9, 2001, now U.S. Pat. No. 7,038,010 which claims priority to U.S. Provisional Application No. 60/247,464, filed Nov. 9, 2000, all of which are incorporated herein by reference in their entirety.

REFERENCE TO GOVERNMENT GRANT

The inventions described herein were supported, at least in part, by the National Institutes of Health Grants R01 DE 06065 and R01 AR 39876. The United States government has certain rights in the invention.

FIELD OF THE INVENTION

The inventions relate to agents and methods for promoting bone deposition and growth in a mammalian subject. These agents and methods are particularly suited for use in mammals with diseases or disorders involving bone loss, such as osteoporosis, osteopenias, fractures, and bone necrosis.

BACKGROUND OF THE INVENTION

There are a variety of diseases which have an adverse impact on bone, including osteoporosis, hypercalcemia of malignancy, osteopenia due to bone metastases, periodontal disease, hyperparathyroidism, periarticular erosions in rheumatoid arthritis, Paget's disease, immobilization-induced osteopenia, loosening of bone prostheses and glucocorticoid treatment. A characteristic feature shared by each of these diseases is bone loss. In some cases, this bone loss is thought to result from an imbalance between bone resorption (breakdown) and bone formation. Bone loss occurs in a wide range of subjects including aging men and women, post-menopausal women, patients who have undergone hysterectomy, patients who are undergoing or have undergone long-term administration of corticosteroids, patients suffering from Cushing's syndrome, and patients having gonadal dysgenesis.

Peak bone mass is usually attained between the ages of 35 and 40 in humans. Thereafter, a slight imbalance occurs between the processes of bone formation by osteoblasts and bone resorption by osteoclasts. This imbalance continues throughout the remainder of the individual's life, at the rate of about 10% per year on the average. However, the rate of bone turnover differs from site to site. For example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk. This imbalance is increased in some diseases, resulting in an even more rapid rate of bone loss, and significant associated problems.

The cells which resorb bone, osteoclasts, and those which make bone, osteoblasts, have very precise functions. The balance between their activities is critical to the maintenance of the skeletal system. Osteoclasts are large, multinucleated cells. They have high capacities for the synthesis and storage of enzymes, including acid hydrolases and carbonic anhydrase isoenzyme II. Activation of osteoclasts to resorb bone is generally thought to involve release of organic acids and membrane-bound packages of enzymes onto the bone surface. This requires elaboration next to the bone surface of a specialized region of the plasma membrane, the ruffled border. In this region the osteoclast's prepackaged, membrane-bound enzymes can fuse with the plasma membrane and be released onto the bone surface in a confined extracellular space. Degradation of the inorganic and organic tissue occurs in this area. The products of resorption are then taken up via endocytosis for additional intracellular processing within cytoplasmic vacuoles. Osteoblasts are mononuclear cells that express and secrete a number of enzymes and structural proteins of the bone matrix, including Type-1 collagen, osteocalcin, osteopontin and alkaline phosphatase (Stein G. et al. Curr Opin Cell Biol (1990) 2: 1018–27). Osteoblasts also synthesize a number of growth regulatory peptides which are stored in the bone matrix, and are presumably responsible for normal bone formation.

Unchecked, bone loss can lead to osteoporosis or osteopenia. Osteopenia is reduced bone mass due to a decrease in the rate of osteoid synthesis to a level insufficient to compensate for normal bone lysis. Osteoporosis is a major debilitating disease whose prominent feature is the loss of bone mass (decreased density and enlargement of intertrabecular spaces) without a reduction in bone volume, producing porosity and fragility. Osteoporosis and osteopenia are present in both aging men and women, due to age-related bone loss. There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

There are currently no satisfactory pharmaceutical approaches to managing bone loss. Bone deterioration associated with post-menopausal osteoporosis has been decreased or prevented with hormones. Although the administration of estrogens have beneficial effects on bone when given even at very low levels, long-term estrogen therapy has been implicated in a variety of disorders. These include an increase in the risk of uterine and breast cancer, vaginal bleeding, and endometrial hyperplasia, and cause many women to avoid this form of treatment. Recently suggested therapeutic regimens which seek to lessen the cancer risk, such as administering combinations of progestogen and estrogen, may be linked to negative cardiovascular effects. Concerns over the significant undesirable effects associated with estrogen therapy, and the limited ability of estrogens to reverse existing bone loss, support the need to develop alternative therapy for bone loss that generates the desirable effects on bone but does not cause undesirable effects.

Antiestrogens, which interact with the estrogen receptor, have been used in women suffering from the effects of osteoporosis, for whom estrogen therapy is not appropriate. This form of therapy has had limited success, perhaps due to the fact that these compounds generally display a mixed agonist/antagonist effect. That is, although these compounds can antagonize estrogen interaction with the receptor, the compounds themselves may cause estrogenic responses in those tissues having estrogen receptors. Therefore, some antiestrogens, when administered alone, are subject to the same adverse effects associated with estrogen therapy. A further disadvantage to both estrogen and antiestrogen therapy is that neither has been shown to promote re-growth of lost bone.

Treatments used for bone loss in both men and women include vitamin and mineral supplementation with calcium and vitamin D. This approach has shown limited effectiveness in treating osteopenias or osteoporosis and the benefits are limited in treating and preventing bone loss. Growth of new bone is not possible with this form of treatment. Bone loss in men is also treated with androgens such as testosterone. Treatment with testosterone also displays antagonistic effects as with estrogen therapy in women, and can lead to baldness, acne, lowering of HDL cholesterol (the "good" cholesterol) and raising of LDL cholesterol (the "bad" cholesterol), and importantly may be associated with an increased risk of prostate cancer and benign prostatic hyperplasia.

Treatment with bisphosphonates such as alendronate, currently marketed by Merck & Co., Inc. as FOSAMAX®, has also been successful in inhibiting bone loss and increasing bone density. However, bisphosphonates have low bioavailability and their administration must avoid food interactions. Treatment with shots or intranasal Calcitonin and low dose PTH (parathyroid hormone) shots have also been employed in an effort to inhibit bone loss and treat or prevent osteoporosis. A detractor from the possible benefits of treatment with calcitonin is the associated high rate of allergic reaction in subjects.

In view of the deficiencies of the currently-available therapies, it is desirable to have new therapeutic methods and agents that promote bone deposition and growth.

SUMMARY OF THE INVENTION

In one aspect, the present invention provides agents for promoting bone deposition and growth in a mammalian subject. The agents are O-glycosylated and non-glycosylated peptides that are derived from vitamin D binding protein, collectively referred to hereinafter as "DBP" peptides. The DBP peptides are from 3 to 18, preferably from 4 to 14 amino acids in length and comprise a sequence which is at least 80% identical, preferably at least 90% identical to the amino acid sequence of a fragment contained within domain III of DBP. In one embodiment, referred to hereinafter as "fADP", the peptide is fourteen amino acids in length and comprises SEQ ID NO. 1. The O-glycosylated form of fADP comprises a sugar residue, preferably an N-acetyl galactosamine, which is attached to the threonine residue at position 3 in SEQ ID NO.1. In other embodiments, the DBP peptides are 4, 5, 6, 7, 8, 10, 11, 12, and 13 amino acids in length and comprise, respectively, the first 4, 5, 6, 7, 8, 10, 11, 12, and 13 amino acids in SEQ ID NO. 1. The DBP peptides are useful for stimulating bone growth and deposition in mammals. Thus, the DBP peptides are useful for the treatment of skeletal disorders such as osteoporosis or osteogenesis imperfecta. The present invention also relates to pharmaceutical compositions comprising the DBP peptides.

In another aspect, the present invention provides a method promoting bone deposition in a subject in need of the same. The method comprises administering to the subject a therapeutically effective quantity of an agent selected from the group consisting of an activated form of vitamin D binding protein referred to hereinafter as "ADBP", one or more DBP peptides, and combinations thereof. The agents may be administered locally to treat specific bone-related disorders or injuries. Local injections may assist in long-bone fracture repair, particularly delayed unions or non-unions of long bone fractures. Alternatively, the agents may be administered systemically to treat bone diseases such as osteopenias that result from other diseases or disease treatments, such as bone loss associated with long-term dialysis, or osteopenia associated with cancers and their treatments. Whether administered systemically or locally, the agents may be useful to generate bone in segmented defects, reconstruction of bone after tumor removal, to achieve spine and other joint fusion, and to achieve bone growth at sites of bone loss due to avascular necrosis.

DESCRIPTION OF THE FIGURES

FIG. 1 is the structural formula for the glycosylated form of fADP, a fourteen amino acid peptide which induces bone formation or deposition in mammalian animals.

DETAILED DESCRIPTION OF THE INVENTION

Bone Structure

Figure 2:
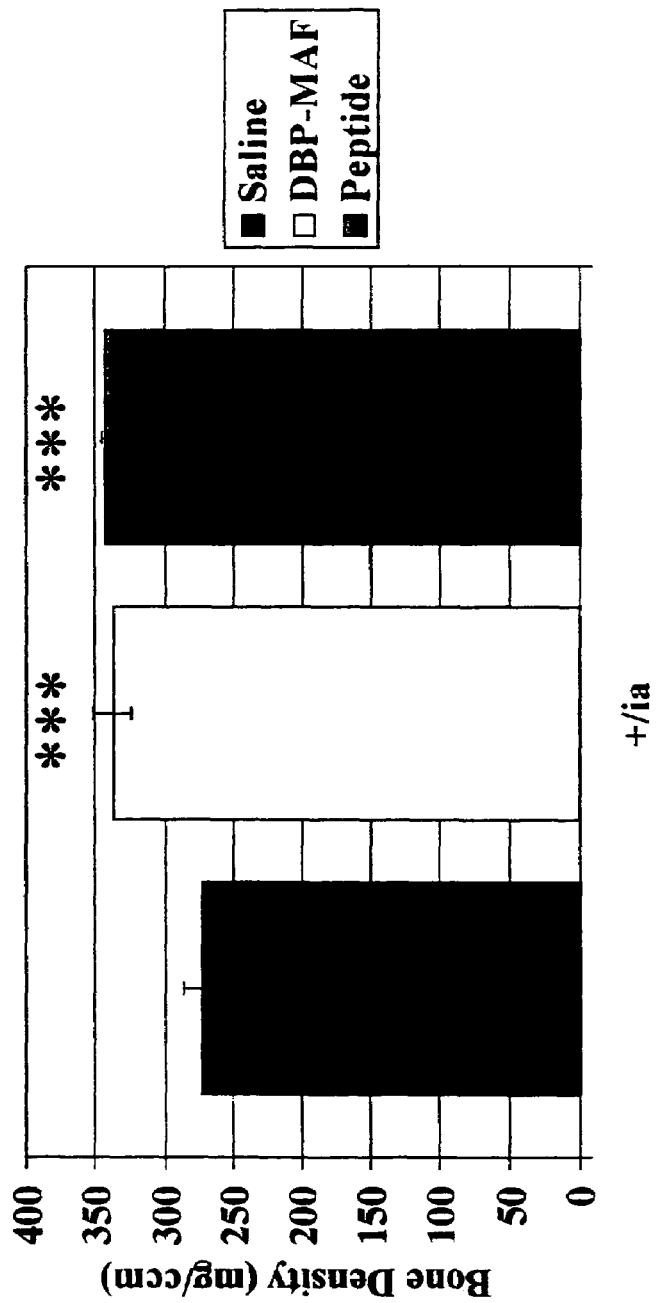
FIG. 2 is a bar graph showing the total bone density in saline, ADBP and DBP peptide treated normal newborn rats receiving saline, 2 ng/g body weight of ADBP, or 0.4 ng/g body weight of fADBP, respectively, every two days for two weeks.

Bone tissue consists of a matrix of collagen (protein) fibers impregnated with mineral (calcium hydroxyapatite). Bone is generally classified into two types: cortical bone, also known as compact bone, and trabecular bone, also known as cancellous or spongy bone. These two types are classified as on the basis of porosity and the unit microstructure. Cortical bone is much denser with a porosity ranging between 5% and 10%. Cortical bone is found primarily in the shaft of long bones and forms the outer shell around cancellous bone at the end of joints and the vertebrae. Trabecular bone is much more porous with porosity ranging anywhere from 50% to 90%. It is found in the end of long bones, in vertebrae and in flat bones like the pelvis. Its basic first level structure is the trabeculae.

Definitions

The term "vitamin D-binding protein" or "DBP" as used herein means the genetically polymorphic glycoprotein vitamin D-binding protein, also known as "group specific component" ("Gc") in humans, including all genetic variations thereof. The singular expression "DBP" is thus understood to encompass all such variants, unless stated otherwise.

The term "activated vitamin D-binding protein", "activated DBP" or "ADBP" as used herein means DBP which has been converted to a macrophage activating factor by the action of certain glycosidases.

The term "trabecular" as used herein refers to cancellous bone consisting of thin plates or spicules with thickness ranging from 50 to 400 mm. These plates are interconnected in a honeycomb pattern.

The term "osteoid" as used herein refers to the organic matrix produced by osteoblasts.

The term "osteocalcin" as used herein refers to a non-collagenous protein secreted by osteoblasts forming a portion of the bone matrix. Elevated levels of osteocalcin in bones of animals treated with agents of the present invention as compared to control animals are indicative of increased levels of bone formation in the agent-treated animals.

The term deoxypyridinoline (Dpd) as used herein refers to an organic protein that is a catabolic product of type I collagen which makes up approximately 90% of the organic bone matrix. Lower levels of Dpd in urine or serum of animals treated with agents of the present invention as compared to control animals are indicative of a decrease in bone resorption in the agent-treated animals.

ADBP

ADBP is the activated form of vitamin D-binding protein ("DBP"), which is an evolutionary conserved but genetically polymorphic plasma glycoprotein present in the $\alpha_2$-globulin fraction of sera. DBP from animals serologically cross-reacts with human DBP. DBP normally constitutes about 0.5% of the plasma proteins in animals. The plasma concentration is generally about 260 µ.g/ml. Native DBP carries a single oligosaccharide moiety containing galactose and sialic acid as dibranched termini at N-acetylgalactosamine. Portions of the oligosaccharide are readily removable by treatment with readily available glycosidases. These glycosidases are equivalent to the functions of B and T cells upon DBP.

Polymorphism in DBP is expressed, both in the oligosaccharide moiety and in the polypeptide portion of the glycoprotein. Polymorphism of the human DBP, known as "group specific component" or "Gc protein", is demonstrable by gel electrophoretic analysis, which reveals two major phenotypes: Gc1 and Gc2. The DBPgs and DBPgm phenotypes (Gc1 in humans) differ from the DBPg phenotype (Gc2 in humans) by four amino acids at positions 152, 311, 416 and 420. The entire nucleotide coding sequences of the Gc1 and Gc2 genes, and the predicted amino acid sequences, have been reported in the literature (Cooke, et al., J. Clin. Invest. 76:2420, 1985; Yang et al., Proc. Natl. Acad. Sci. USA 82:7994, 1985). Gc1 is further divided into Gc1f and Gc1s subtypes which migrate electrophoretically as two bands, "fast" and "slow", (Svasti et al., Biochem. 18:1611, 1979).

According to U.S. Pat. Nos. 5,177,001 and 5,177,002 to Nobuto Yamamoto, the entire disclosures of which are incorporated herein by reference, DBP phenotypes and subtypes are characterized as glycoproteins. As further described by Yamamoto, DBP is activated to ADBP with (i) β-galactosidase, or (ii) β-galactosidase in combination with sialidase, α-mannosidase, or a mixture thereof. DBPg treated with β-galactosidase alone results in removal of galactose and the formation of activated DBP. Conversion of DBPgs to the activated form requires incubation with the combination of β-galactosidase and sialidase. DBPgm conversion requires β-galactosidase and α-mannosidase. Activated DBP thus comprises a protein having substantially the amino acid sequence of DBP and a terminal N-acetylgalactosamine group. The glycosylation is in DBP domain III, in the vicinity of amino acid 420. Domain III comprises a region of DBP from about Ser-373 to the COOH-terminus at Ser-460. According to Yamamoto, the glycosylation occurs at Thr(418) in human DBPg (Gc2), or Thr(418) (or Thr (420)) in DBPgs/gm, or Ser(418) in those species of DBPg, such as rat and mouse DBPg, which contain serine at position 418 in lieu of threonine. The amino acid sequence of one form of human DBP was published in Schoentgen, F. et al. (1995) Biochimica et Biophysica Acta 871: 189–198, which is specifically incorporated herein by reference.

DBP may be isolated from the blood using 25-hydroxyvitamin $D_3$-SEPHAROSE® (agarose beads) affinity chromatography according to the procedure of Link et al., Anal. Biochem. 157, 262 (1986). DBP may also be purified by actin-agarose affinity chromatography according to the procedure of Haddad et al., Biochem. J. 218, 805 (1984), which takes advantage of the binding specificity of DBP for actin.

DBP is then converted to ADBP by chemical treatment or treatment with glycosidases. As described by Yamamoto, about 0.1 units (1 unit being the amount of enzyme which catalyzes 1.mu.mole of substrate in 1 minute) of each enzyme per 1 μg of DBP in phosphate buffer is sufficient for this purpose. The temperature may vary from 25° C. to 37° C., with about 37° C. being preferred. A reaction time of about 30 minutes at 37° C. is generally sufficient to obtain complete conversion of DBP to the glycosylated form of ADBP. Preferably, all enzymes are most advantageously contained in the solid phase. For example, the enzymes may be fixed to agarose beads with a suitable coupling agent such as cyanogen bromide. Methods for attaching enzymes to solid supports are known to those skilled in the art.

For further discussions regarding the conversion of DBP to the potent macrophage activator form see Yamamoto and Homma, Proc. Natl. Acad. Sci. USA 88, 8539–8543, 1991; Homma et al., Immunol. Cell Biol., 249–257, 1993; Yamamoto and Kumashiro, J. Immunol. 151, 2794–2802, 1993; and Yamamoto U.S. Pat. Nos. 5,177,001 and 5,177,002.

DBP Peptides

The DBP peptides are peptide fragments of domain III of ADP or biologically active equivalents thereof. In one embodiment, the DBP peptide, which is referred to hereinafter as fADBP, comprises the amino acid sequence set forth in SEQ ID NO. 1. The DBP peptides are from 3 to 18, preferably from 4 to 14 amino acids in length. Preferably, the sequences of the DBP peptides which are from 3 to 11 amino acids in length comprise the first 3, 4, 5, 6, 7, 8, 10, and 11, respectively of SEQ ID NO. 1. The DBP peptides which are from 12 to 18 amino acids in length comprise a sequence which is at least 70%, preferably at least 80%, more preferably at least 90% identical to sequences, referred to hereinafter as "reference sequences", of fragments that are located within domain III of DBP. The third amino acid in each reference sequence is the threonine (Thr) that is normally glycosylated in DBP.

Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program. As used herein the term "biologically active equivalent" refers to a DBP peptide whose sequence whose is not 100% identical to a reference sequence but retains the ability to increase total bone density when administered at a concentration of 0.4 ng/g body weight every other day for two weeks to an adult rat.

The DBP peptides whose sequences are not identical to a particular reference sequence comprise substitutions within the reference sequence. While it is possible to have nonconservative amino acid substitutions, it is preferred that, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

The term DBP peptide as used herein encompasses peptides that are non-glycosylated and peptides that further comprise at least one sugar residue, preferably a sugar amine, more preferably an N-acetyl galactosamine attached to the threonine or serine residue located at position 3 of the DBP peptide. DBP peptides may be made using standard techniques and may be obtained commercially.

Table 1 below provides examples of DBP peptides which comprise sequences that are identical to references sequences that are from 3 to 14 amino acids in length, as well as DBP peptides whose sequences are a modified version of SEQ ID NO. 1. The modified sequences comprise from 1 to 4 amino acid substitutions in SEQ ID NO. 1.

```
N-Thr  Pro  Thr  Glu  Leu  Ala  Lys  Leu  Val  Asn  Lys  Arg  Ser  Glu-C
N-Thr  Pro  Thr  Glu  Leu  Ala  Lys  Leu  Val  Asn  Lys  Arg  Ser
N-Thr  Pro  Thr  Glu  Leu  Ala  Lys  Leu  Val  Asn  Lys  Arg
N-Thr  Pro  Thr  Glu  Leu  Ala  Lys  Leu  Val  Asn  Lys
N-Thr  Pro  Thr  Glu  Leu  Ala  Lys  Leu  Val  Asn
N-Thr  Pro  Thr  Glu  Leu  Ala  Lys  Leu  Val
N-Thr  Pro  Thr  Glu  Leu  Ala  Lys  Leu
N-Thr  Pro  Thr  Glu  Leu  Ala  Lys
N-Thr  Pro  Thr  Glu  Leu  Ala
N-Thr  Pro  Thr  Glu  Leu
N-Thr  Pro  Thr  Glu
N-Thr  Pro  Thr  Glu  Leu  Ala  Lys  Leu  Val  Asn  Lys  Arg  Ser  Asp-C
N-Thr  Pro  Thr  Glu  Leu  Ala  Lys  Leu  Val  Asn  Lys  Arg  Cys  Gln-C
N-Thr  Pro  Thr  Glu  Leu  Ala  Lys  Leu  Val  Asn  Lys  Lys  Ser  Glu-C
N-Thr  Pro  Thr  Glu  Leu  Ala  Lys  Leu  Val  Asn  Lys  Arg  Ser  Glu-C
N-Thr  Pro  Thr  Glu  Leu  Ala  Lys  Leu  Val  Asn  Arg  Arg  Ser  Glu-C
N-Thr  Pro  Thr  Glu  Leu  Ala  Lys  Leu  Val  Gln  Lys  Arg  Ser  Glu-C
N-Thr  Pro  Thr  Glu  Leu  Ala  Lys  Leu  Leu  Asn  Lys  Arg  Ser  Glu-C
N-Thr  Pro  Thr  Glu  Leu  Ala  Lys  Leu  Ile  Asn  Lys  Arg  Ser  Glu-C
N-Thr  Pro  Thr  Glu  Leu  Ala  Lys  Val  Val  Asn  Lys  Arg  Ser  Glu-C
N-Thr  Pro  Thr  Glu  Leu  Gly  Lys  Leu  Val  Asn  Lys  Arg  Ser  Glu-C
N-Thr  Pro  Thr  Glu  Leu  Ser  Lys  Leu  Val  Asn  Lys  Arg  Ser  Glu-C
N-Thr  Pro  Thr  Glu  Leu  Thr  Lys  Leu  Val  Asn  Lys  Arg  Ser  Glu-C
N-Thr  Pro  Thr  Glu  Leu  Val  Lys  Leu  Val  Asn  Lys  Arg  Ser  Glu-C
N-Thr  Pro  Thr  Glu  Ile  Ala  Lys  Leu  Val  Asn  Lys  Arg  Ser  Glu-C
N-Thr  Pro  Thr  Glu  Val  Ala  Lys  Leu  Val  Asn  Lys  Arg  Ser  Glu-C
N-Thr  Pro  Thr  Glu  Gly  Ala  Lys  Leu  Val  Asn  Lys  Arg  Ser  Glu-C
N-Thr  Pro  Ser  Glu  Leu  Ala  Lys  Leu  Val  Asn  Lys  Arg  Ser  Glu-C
N-Thr  Pro  Thr  Glu  Val  Gly  Lys  Val  Ala  Asn  Lys  Arg  Ser  Asp-C
N-Thr  Pro  Thr  Glu  Ala  Gly  Lys  Ala  Ala  Asn  Lys  Arg  Ser  Asp-C
N-Thr  Pro  Thr  Glu  Gly  Gly  Lys  Ala  Ala  Asn  Lys  Arg  Ser  Asp-C
N-Thr  Pro  Thr  Glu  Gly  Gly  Lys  Ala  Gly  Asn  Lys  Arg  Ser  Asp-C
N-Thr  Pro  Thr  Glu  Ile  Ala  Lys  Ile  Val  Asn  Lys  Arg  Ser  Glu-C
N-Thr  Pro  Thr  Glu  Ile  Gly  Lys  Ile  Ala  Asn  Lys  Arg  Ser  Asp-C
N-Thr  Pro  Thr  Glu  Leu  Ala  Lys  Leu  Val  Asn  Lys  Arg  Ser  Glu-C
N-Thr  Pro  Thr  Glu  Leu  Val  Arg  Leu  Leu  Gln  Arg  Arg  Thr  Glu-C
N-Thr  Pro  Thr  Glu  Leu  Ala  Lys  Leu  Leu  Gln  Lys  Arg  Thr  Glu-C
N-Thr  Pro  Thr  Glu  Leu  Ile  Lys  Leu  Ile  Gln  Lys  Arg  Thr  Glu-C
N-Thr  Pro  Thr  Glu  Leu  Ala  Lys  Leu  Leu  Asn  Lys  Arg  Cys  Glu-C
N-Thr  Pro  Thr  Glu  Leu  Ala  Lys  Ile  Ile  Asn  Lys  Arg  Cys  Glu-C
```

```
                         -continued
N-Thr Pro Thr Glu Leu Cys Lys Leu Val Asn Lys Arg Ser Glu-C N-Thr Pro Thr Glu Leu Ser Lys Leu Ser Asn Lys Arg Cys Glu-C N-Thr Pro Thr Glu Leu Ala Lys Leu Thr Asn Lys Arg Cys Glu-C N-Thr Pro Thr Glu Leu Ser Lys Leu Val Asn Lys Arg Cys Glu-C N-Thr Pro Thr Glu Leu Ser Lys Leu Ile Asn Lys Arg Ser Glu-C N-Thr Pro Thr Glu Leu Ser Lys Leu Leu Asn Lys Arg Cys Glu-C
```

Use of the DBP Peptides

The DBP peptides and ADBP have application in the healing of bone fractures and defects in humans and other animals. Pharmaceutical compositions comprising the DBP peptides or ADBP have prophylactic use in closed as well as open fracture reduction and also in the improved fixation of artificial joints. De novo bone formation induced by such an osteoinductive or osteogenic agent contributes to the repair of congenital, trauma induced, or oncologic resection induced defects, and also is useful in cosmetic plastic surgery.

The DBP peptides and ADBP may be used in the treatment of periodontal disease, and in other tooth repair processes. Such anabolic agents may provide an environment to attract bone-forming cells, stimulate growth of bone-forming cells or induce differentiation of progenitors of bone-forming cells, and may also support the regeneration of the periodontal ligament and attachment apparatus, which connects bone and teeth.

The DBP peptides and ADBP may also be useful in the treatment of osteoporosis and osteogenesis imperfecta. The DBP peptides and ADBP may be used in prevention/reversal of osteoarthritis. The proteins and polypeptides of the invention may also be used in bone-involved wound healing and related repair.

Animal Models for Evaluating the Effects the DBP Peptides and Determining the Dosage of the DBP Peptides and ADBP Animal models are recognized as invaluable tools for identifying proteins and peptides which are effective at increasing bone density and bone formation. Animal models are also invaluable tools for determining effective doses of such agents.

In accordance with the present invention, the effect of ADBP and fADBP in bone tissue has been demonstrated using normal newborn and adult rats.

Dosage

The DBP peptides and ADBP, or combinations thereof are administered to a host subject in a therapeutically effective amount. As used herein, the term "therapeutically effective amount" means the total amount of the anabolic agent that is sufficient to show a meaningful benefit, i.e., an increase in total bone density, total bone content, total bone area, trabecular bone density, trabecular bone content, trabecular bone area, cortical bone density, cortical bone content, or cortical bone area.

The amount of the agents required will depend upon the nature and severity of the condition being treated, and on the nature of prior treatments which the subject has undergone and the type of defect or disease being targeted. Ultimately, the dosage will be determined using clinical trials. Initially, the clinician will administer doses that have been derived from animal studies.

In accordance with the present invention, it has been determined that glycosylated ADBP, and a number of glycosylated and non-glycosylated DBP peptides promote bone deposition and bone growth in mammals. ADBP and the DBP peptides are effective at nanogram levels in stimulating bone deposition in vivo.

Initially, in vitro assays were used to determine the optimal doses of ADBP and fADBP to elicit bone resorption. The concentrations were determined by dose response analysis. Comparable concentrations of the agents were thereafter used in studies undertaken to assess the effect of the agents in osteopetrotic mutant rats and normal rats. Although earlier studies had demonstrated a bone resorptive effect of low doses of ADBP, the in vivo studies revealed the quite unexpected result that, as a function of dose and interval of administration, ADBP exhibits the anabolic effect of promoting bone growth. More precisely, the subsequence studies showed that multiple intermittent injections of relatively high doses of glycosylated ADBP promoted bone growth in animals. These levels are one or two orders of magnitude higher than the previous in vivo testing of ADBP (U.S. Patent NO. Schneider et al 1995, incorporated herein by reference), where ADBP exhibited a bone resorptive effect.

Administration of the DBP Peptides and ADBP

The DBP peptides, ADBP, or combinations thereof may be administered either locally or systemically to treat bone loss disorders in mammals, inclusive of humans. Candidates for human treatment comprise any individuals who have diseases associated with bone loss, for example, women with osteoporosis. For systemic delivery, ADBP may be administered by any convenient route, which will result in delivery to the circulation of an amount of the factor sufficient to induce substantial bone deposition. Any route acceptable for the delivery of proteinaceous pharmaceuticals may be employed. For example, ADBP and the DBP peptides may be given by subcutaneous, intravenous, intraarterial, intraperitoneal or intramuscular injection. The DBP peptides, especially those that are less than 9 amino acids in length, may also be administered orally. Parenteral administration is preferred.

For local administration to a site of bone deficiency, the DBP peptides and ADBP may be given by direct local injection, by continuous infusion via infusion pumps, by implantation of controlled release devices. Local administration may also be achieved by other means such as topical administration in the form of creams or gels comprising one or more DBP peptides, ADBP, or combinations thereof and appropriate carriers.

To minimize any possible immunologic reaction from administration of ADBP and the DBP peptide, it is preferred that the patient would receive only ADBP or a DBP peptide derived from the same species. Similarly, the risk of immunologic reaction in individuals would be minimized by administering only the same variant of ADBP or the DBP peptide, such as in situations wherein there is intraspecies ADBP or DBP peptide polymorphism. However, the risk of immune reaction from cross-species administration of ADBP and the DBP peptide is believed minimal due to the high level of evolutionary conservation in that molecule. As demonstrated hereinafter, rats tolerated treatment with human ADBP and DBP peptides.

ADBP and the DBP peptides may be taken up in pharmaceutically acceptable carriers, particularly those carriers suitable for delivery of proteinaceous pharmaceuticals. The factor is soluble in water or saline solution. Thus, the preferred formulation for veterinary pharmacological use comprises a saline solution of the agent. The formulation may optionally contain other agents, such as agents to maintain osmotic balance. For example, a typical carrier for injection may comprise an aqueous solution of 0.9% NaCl or phosphate buffered saline (a 0.9% NaCl aqueous solution containing 0.01 M sodium phosphate, pH 7.0). The amount of active compound in the formulation is such that a suitable dosage will be obtained.

The amount of ADBP or DBP peptide administered depends on a variety of factors, including the potency of the preparation, the size and weight of the subject, the extent of the affliction, and the like. A dosage of as little as 0.4 microgram per kg has been shown to result in bone deposition. A representative treatment regimen may comprise, for example, from about 20 µg to about 30 µg of a DBP peptide or from 20 µg to about 100 µg ADP, administered parenterally on an intermittent basis, e.g. every second day. It is contemplated that treatment would extend indefinitely or until satisfactory correction of the disease or disorder is demonstrated.

The efficacy of therapy with the anabolic agents of the present invention can be noninvasively monitored through visualization of the marrow cavity using skeletal densitometry or skeletal X-ray. These procedures are capable of indicating an increase in bone mass. Invasive monitoring of therapy may be carried out by periodic bone biopsy, such as from the iliac crest of the pelvis bone. The bone is fixed and the tissue prepared in the same manner as in the post mortem bone biopsies of ADBP and the DBP peptide-treated rats described in the examples below.

The duration of therapy using ADBP and/or the DBP peptide will vary, depending on the severity of the disease being treated and the condition and response of each individual patient. Ultimately the attending physician will decide on the appropriate duration of therapy using the pharmaceutical composition of the present invention.

The invention is illustrated by the following non-limiting examples.

EXAMPLE 1

Systemic Administration of ADBP to Newborn Animals

ADBP, at a dosage of 2.0 ng/g of body weight, was administered by intraperitoneal injection into normal newborn rats every two days for two weeks.

EXAMPLE 2

Systemic Administration of fADBP to Newborn Animals

Glycosylated fADBP, at a dosage of 0.4 ng/g of body weight, was administered by intraperitoneal injection into normal newborn rats every two days for two weeks.

Results

The effect of the above-described treatments on bone density, bone circumference, and the rate of bone resorption were evaluated. Normal rats receiving saline injections served as controls.

After humane sacrifice, long bones were collected from rats subjected to agent treatment as described in Examples 1 and 2. The bones were evaluated using densitometry techniques with the Norland Medical Systems pQCT scanner. The densitometric parameters that were determined included:

1. Total Content, which is the mineral content of the bone within a 1 mm slice.
2. Total Density, which is the mean density of the total bone.
3. Trabecular Content, which is the mineral content of the trabecular bone within a 1 mm slice.
4. Trabecular Density, which is the mean density of the trabecular bone
5. Cortical Content, which is the mineral content of the cortical bone within a 1 mm slice.
6. Cortical Density, which is the mean density of the total bone.
7. Periosteal circumference in the "circular ring model" in mm.
8. Endosteal circumference in the "circular ring model" in mm.
9. Total area ($mm^2$), which is the cross sectional area of the bone after the soft tissue has been peeled off.
10. Cortical area ($mm^2$), which is the area assigned to be pure cortical.
11. Trabecular area ($mm^2$), which is the cross sectional area of the trabecular area after the cortical and subcortical area has been peeled off.

Figure 3:
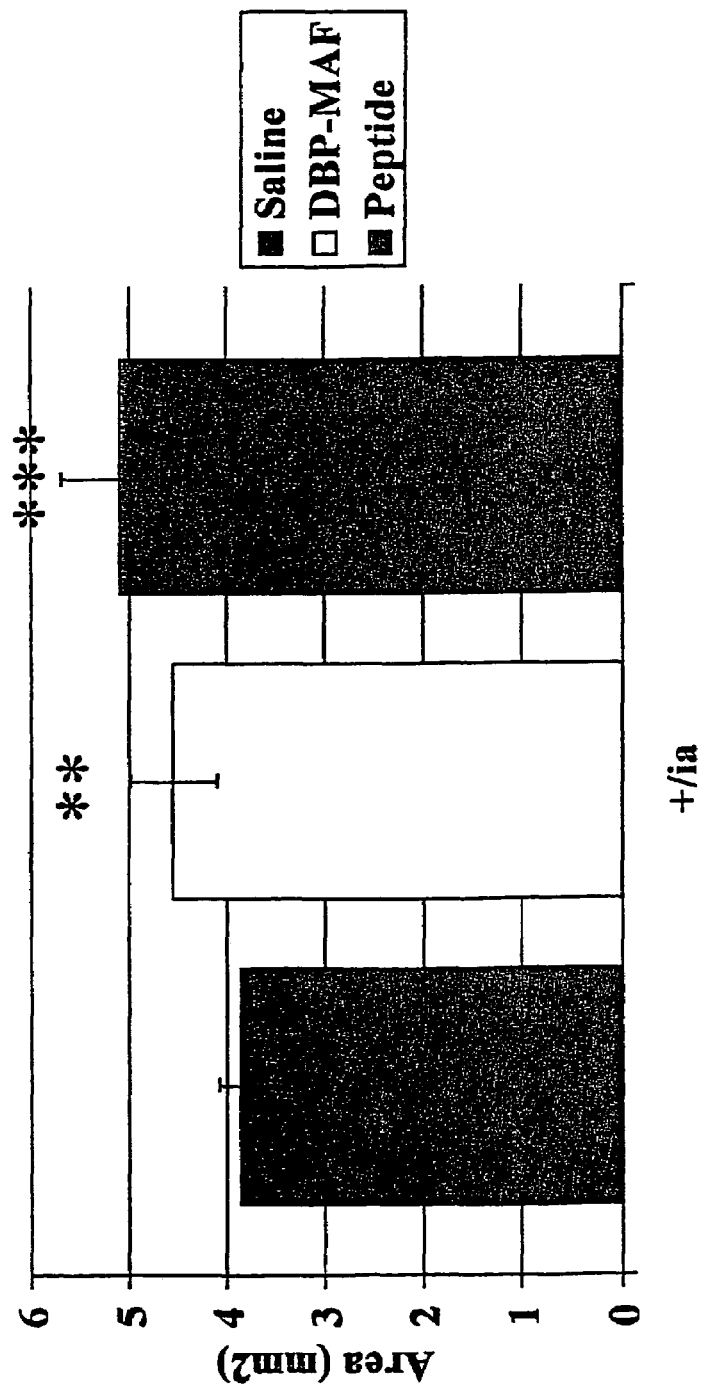
FIG. 3 is a bar graph showing the total bone-slice surface area in saline, ADBP and DBP peptide treated normal newborn rats receiving saline, 2 ng/g body weight of ADBP, or 0.4 ng/g body weight of fADBP, respectively, every two days for two weeks.

Effects of Agents on Bone Density:

Data from a representative slice of the proximal tibia was used to demonstrate the effects of ADBP and fADBP on total bone density and total cross sectional area of the bones. The total bone density of both treatment groups was significantly greater than that of the saline treated animals, as shown in FIG. 2. The total surface area of representative bone slices was also significantly increased in both treatment groups as compared to controls, as shown in FIG. 3.

Figure 4:
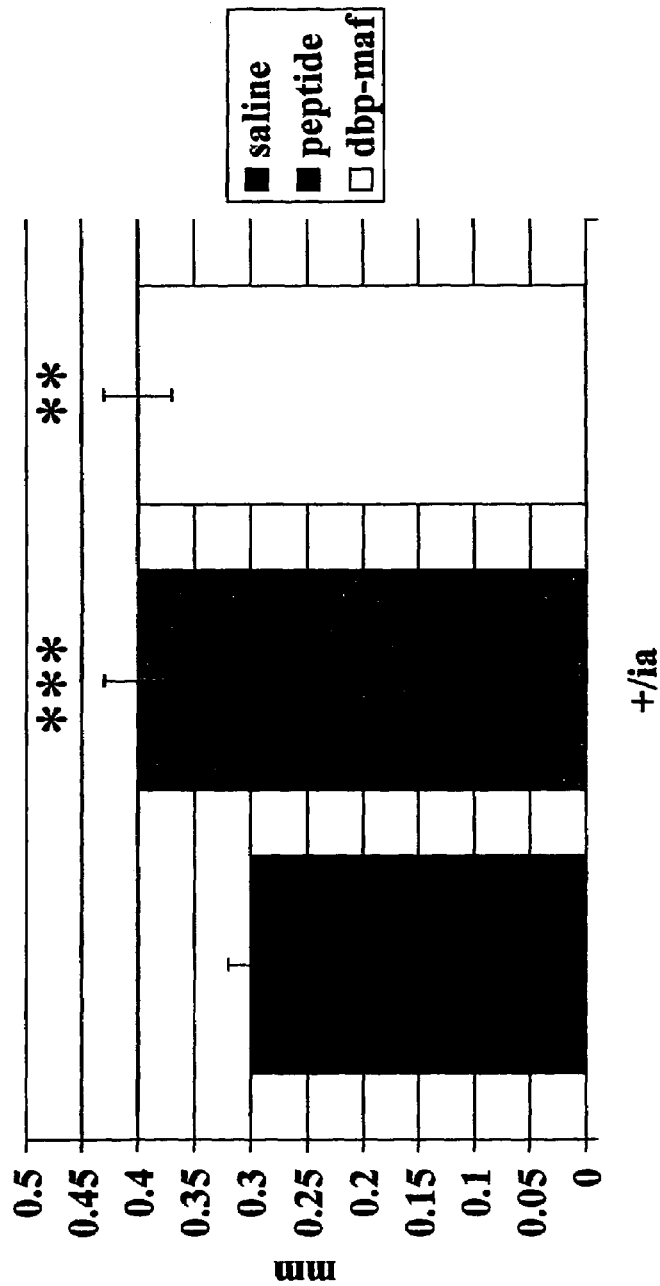
FIG. 4 is a bar graph showing the cortical thickness in saline, ADBP and peptide treated normal newborn rats receiving saline 2 ng/g body weight of ADBP, or 0.4 ng/g body weight of fADBP, respectively, every two days for two weeks.
Figure 5:
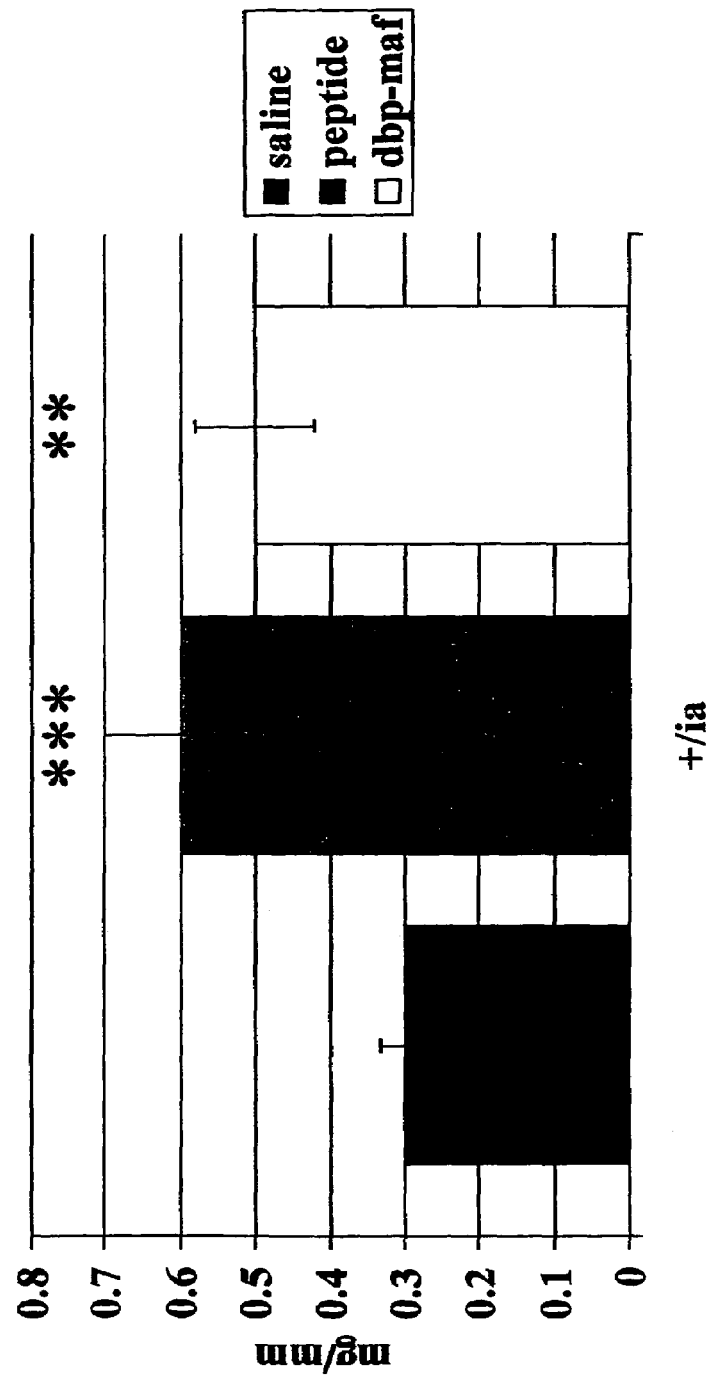
FIG. 5 is a bar graph showing the trabecular content in saline, ADBP and peptide treated normal newborn rats receiving saline 2 ng/g body weight of ADBP, or 0.4 ng/g body weight of fADBP, respectively, every two days for two weeks.
Figure 6:
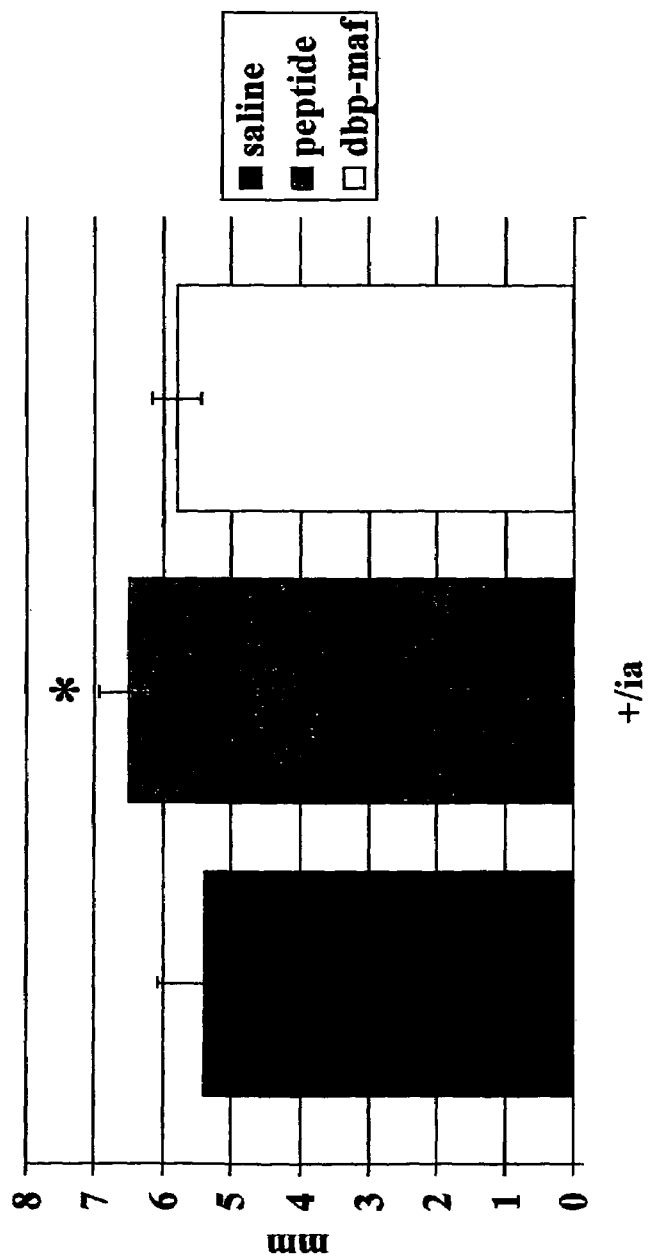
FIG. 6 is a bar graph showing the endosteal circumference in saline, ADBP and peptide treated normal newborn rats receiving saline, 2 ng/g body weight of ADBP, or 0.4 ng/g body weight of fADBP, respectively, every two days for two weeks.
Figure 7:
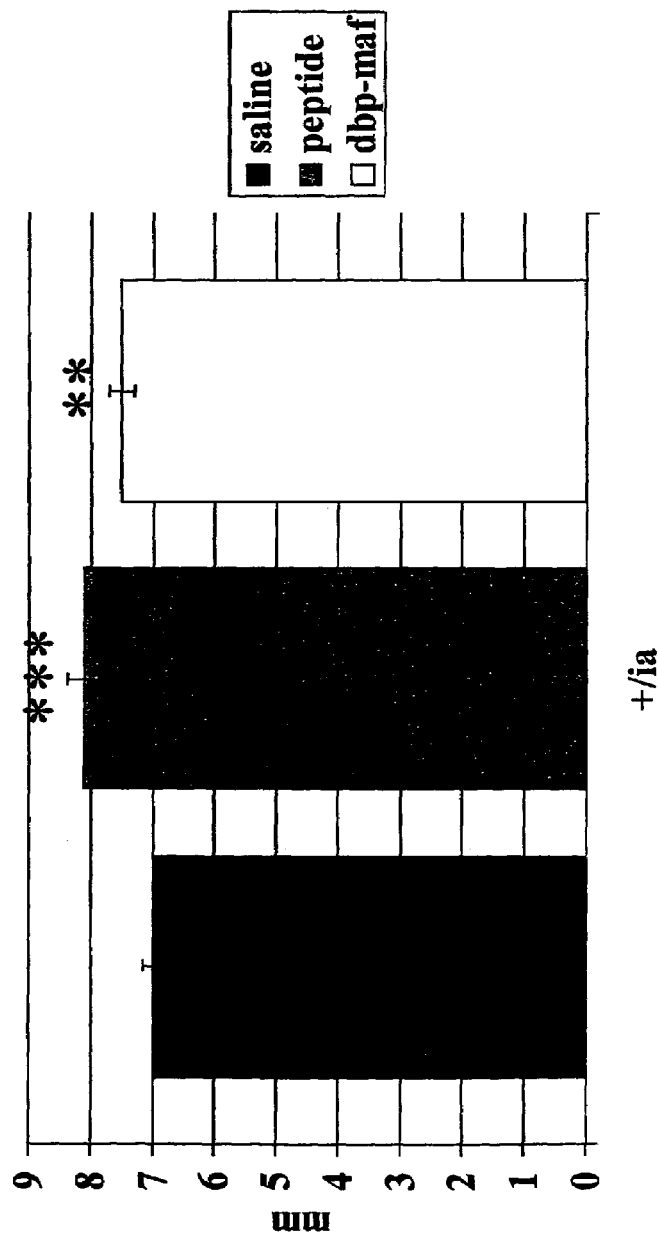
FIG. 7 is a bar graph showing the periosteal circumference in saline, ADBP and peptide treated normal newborn rats receiving saline, 2 ng/g body weight of ADBP, or 0.4 ng/g body weight of fADBP, respectively, every two days for two weeks.
Figure 8:
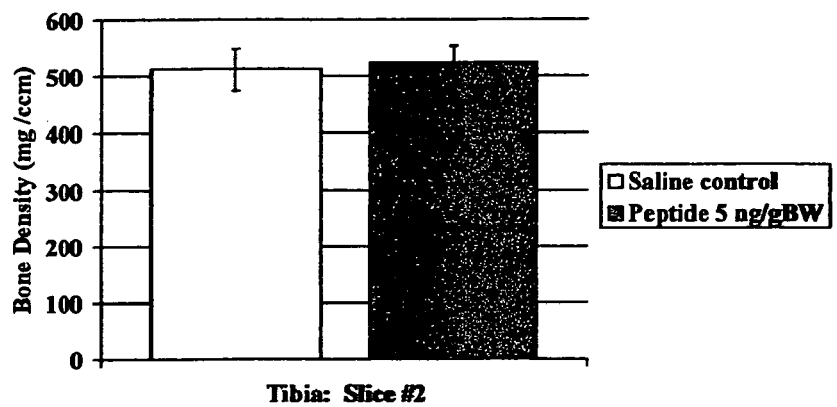
FIG. 8 is a bar graph showing total bone density and cortical bone density in adult animals receiving multiple injections of saline or glycosylated fADBP. Peptide-treated animals received 5.0 ng of fADBP/g of body weight every two days for two weeks.
Figure 8:
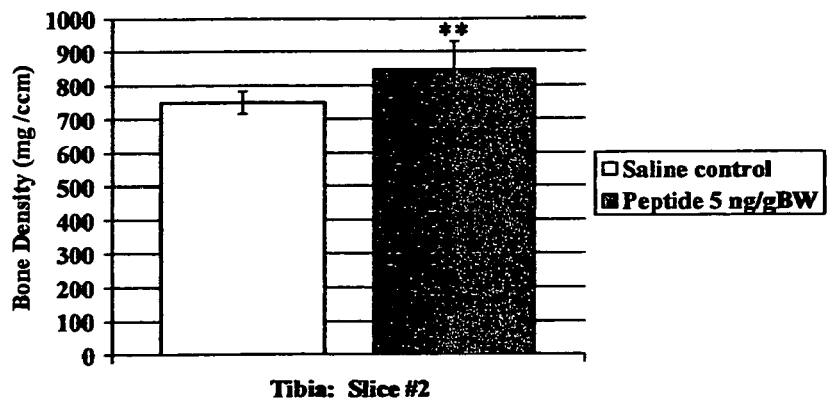
Figure 9:
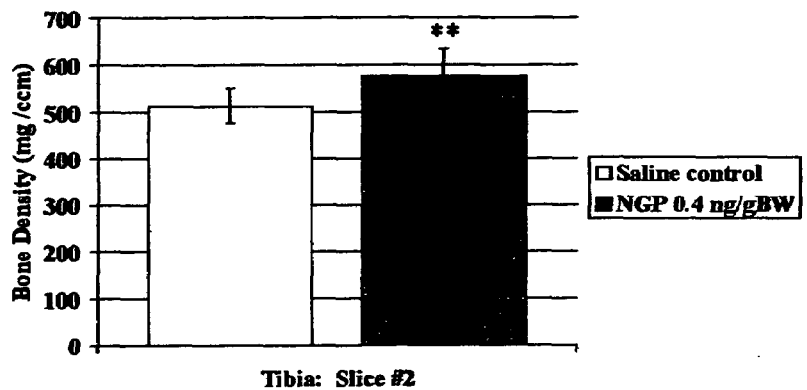
FIG. 9 is a graph showing total bone density and cortical bone density in adult animals receiving multiple injections of saline or non-glycosylated fADBP. Peptide-treated animals received 0.4 ng of fADBP/g of body weight every two days for two weeks.
Figure 9:
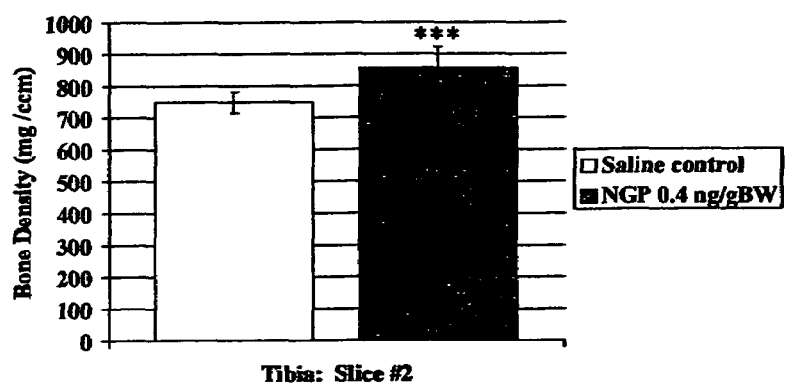

Effects of Agents on Bone Circumference:

The harvested long bones were subjected to further assessment to demonstrate the promotion of bone growth in ADBP and fADBP-treated animals. Using a representative tibial slice, the effect of treatment on cortical thickness (FIG. 4), trabecular content (FIG. 5), endosteal circumference (FIG. 6), and periosteal circumference (FIG. 7) in newborn animals was assessed. Based on our evaluation of each of these parameters, it was revealed that both ADBP and fADBP had a potent effect on bone growth.

Effects of Agents on Bone Resorption:

Urine was collected from rats subjected to treatment as described in Examples 1–3. Deoxypyridinoline (Dpd) was measured in the collected urine. Employing the biochemical assay referred to as Pyrilinks-D, the levels of Dpd crosslinked products were determined to provide a measure of bone collagen degradation. This assay is accepted for evaluation of in vivo bone resorption. The results indicated that the treated with fADP as described above had lower levels of Dpd in their urine than the animals injected with saline alone, suggesting that the DBP peptide had an effect on bone resorption.

EXAMPLE 3

Systemic Administration of fADBP (Without Sugar) to Adult Animals

Non-glycosylated fADBP, at a dosage of 0.4 ng/g of body weight, was administered by subcutaneous injection into normal adult rats every two days for two weeks. The effect of this treatment on bone density and DpD levels was assayed as described above. The results are shown in Table 2 below.

EXAMPLE 4

Systemic Administration of fADBP (With Sugar) to Adult Animals

Glycosylated fADBP, at a dosage of 5.0 ng/g of body weight was administered by subcutaneous injection into normal adult rats every two days for two weeks. The effect of this treatment on bone density was assayed as described above. The results are shown in Table 2 below.

COMPARATIVE EXAMPLES

Administration of Low Doses of ADBP and fADBP and High Doses of fADBP

Rats were treated every four days during a two week evaluation with doses of the ADBP which were from 5 fold to 25 fold lower than the doses used in example 1. A constant amount (0.2 ng) of ADBP was administered to newborn rats every four days for two weeks. During the two week period, the body weight of the animals increased from a value of about 5 grams to a value of about 25 grams. Animals which were treated less frequently with 10 to 50 fold less ADBP exhibited bone resorption rather than bone formation. These results demonstrate that, as reported in U.S. Pat. No. 5,641,747, ADBP exhibits a catabolic effect at very low dosages. Such an effect is in sharp contrast to the unexpected and novel effects reported here relating to the anabolic effect of higher doses of ADBP.

Ovariectomized Sprague-Dawley rats were allowed to lose bone from 60 days. Thereafter, animals were injected with glycosylated fADBP or non-glycosylated fADBP, at concentrations ranging from 100 ng/g of body weight to 30 µg/g of body weight every day for 60 days. Such treatment had no detectable toxic effect and no significant effect on the bone formation in these animals.

| Treatment | Total Bone Density | Deoxypyridinoline (DpD) Pyrilinks-D (bone resorption) | Osteocalcin (bone formation) |
|---|---|---|---|
| 1. DBP-MAF (ADBP) 2 ng/g B.W. every 2 days | increase (highly significant) | no change | — |
| 2. Peptide (fADBP) 0.4 ng/g B.W. every 2 days | increase (highly significant) | decrease (not significant) | — |
| 3. Peptide (fADBP) 0.4 ng/g B.W. every 4 days | decrease (significant) | no change | increase (significant) |
| 4. DBP-MAF (ADBP) 0.2 ng/g B.W. every 4 days | increase (significant) | — | no change |
| 5. DBP-MAF (ADBP) 0.2 ng/injection every 4 days | decrease (significant) | increase (significant) | decrease (significant) |
| 6. Peptide (without sugar) 0.4 ng/g B.W. every 2 days (Adult) | increase (significant) | decrease (highly significant) | no change |
| 7. Peptide (fADBP) 5 ng/g B.W. every 2 days (Adult) | increase (significant) | — | — |

CONCLUSIONS

The anabolic effect of the whole protein DBP-MAF or ADBP is greatest when it is administered at a dose of 2.0 ng/g body weight once every two days. (1) The effect is diminished but still significant when a 10-fold lower dose is administered once every 4 days. (4) The effect is reversed when a constant quantity (0.2 ng/injection) is administered once every 4 days. (5)

The anabolic effect of the 14 amino acid peptide fADBP is greatest when administered at a dose of 0.4 ng/g body weight once every 2 days. (2) If the same dose is administered once every 4 days, there is a decrease in bone density. (3) Because the injections are less frequent, even though the dose was unchanged, the total amount of peptide administered was reduced. The fADBP peptide utilized in experiments 2, 3 and 7 has a single bound sugar. The fADBP peptide without the sugar (6) caused an increase in bone density in adult rats. These results indicate that dosing schedules and concentrations can be optimized using in vivo model systems.

EXAMPLE 5

Moderate-Dose Systemic Administration of Glycosylated fADBP peptide to Newborn Animals Normal newborn rats were administered moderate doses of glycosylated fADBP. fADBP was administered to normal rats in the amount of 0.5 ng/g body weight every two days for a period of two weeks. Control rats were injected with an equal volume of saline. At the conclusion of the treatment period, the animals were humanely sacrificed, and the tibias were harvested for bone densitometry. The results demonstrate that intermittent administration of a moderate dose of glycosylated fADBP every to newborn animals for a period of at least two weeks increased total bone density, trabecular bone density, cortical bone density, total content, trabecular content, cortical content, total area, trabecular area, and cortical area of the tibia. The effects were consistent with the effects obtained when animals were injected with slightly lower doses of fADBP (i.e., 0.4 ng/g body weight every two days for a period of two weeks), and demonstrated the anabolic effects of this DBP peptide.

EXAMPLE 6

Systemic Administration of Nonglycosylated DBP Peptides to Adult Rats

Figure 10:
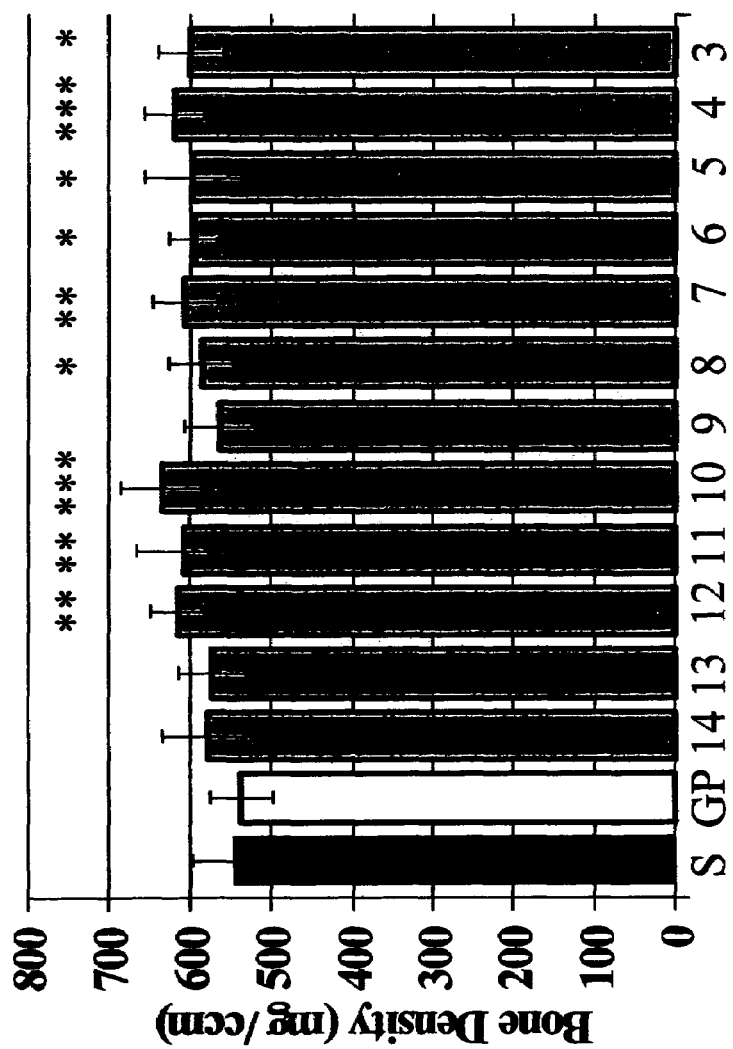
FIG. 10 is a bar graph showing total bone density in adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks. The level of significance is as follows: *=p<0.001; =p<0.01; *=p<0.05.
Figure 11:
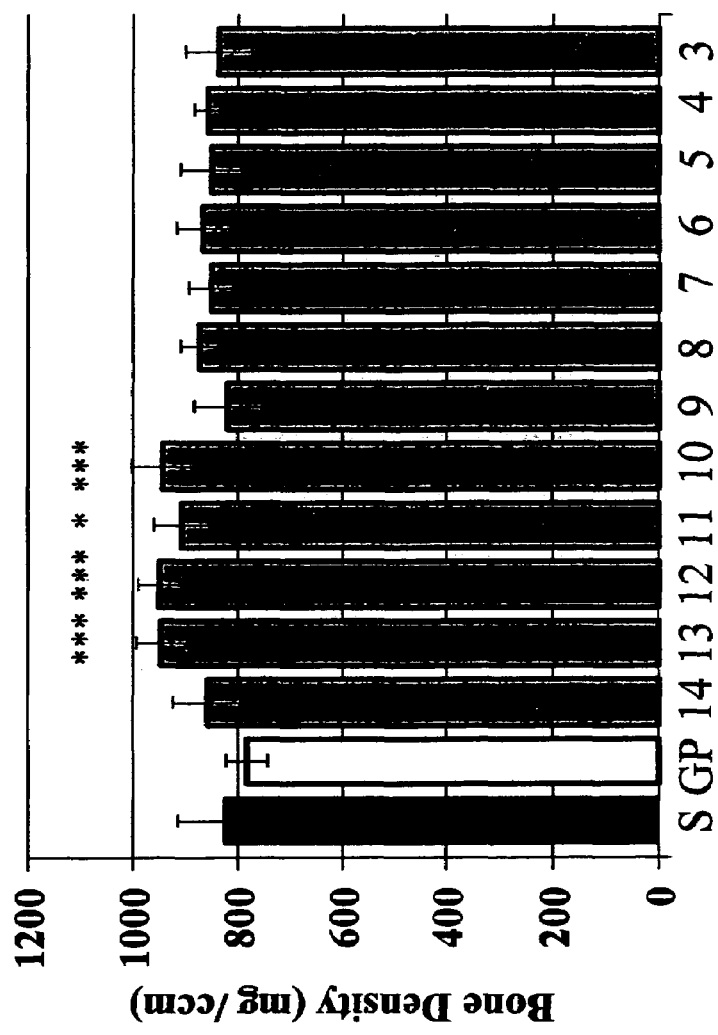
FIG. 11 is a bar graph showing cortical/subcortical bone density in adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.
Figure 12:
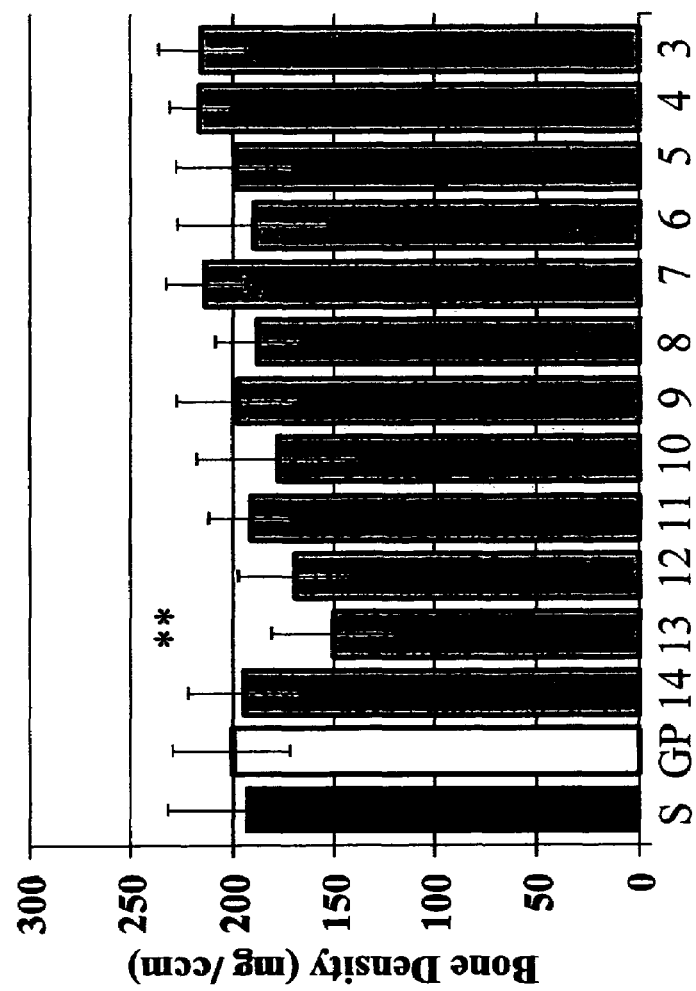
FIG. 12 is a bar graph showing trabecular bone density in adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.
Figure 13:
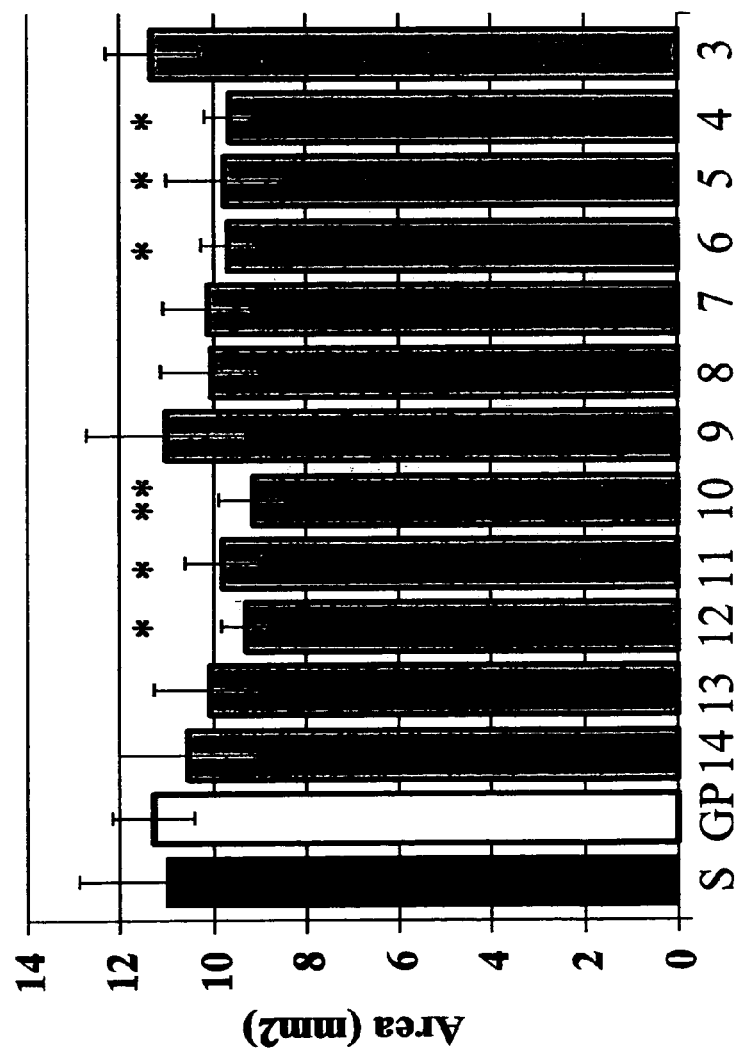
FIG. 13 is a bar graph showing total area of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.
Figure 14:
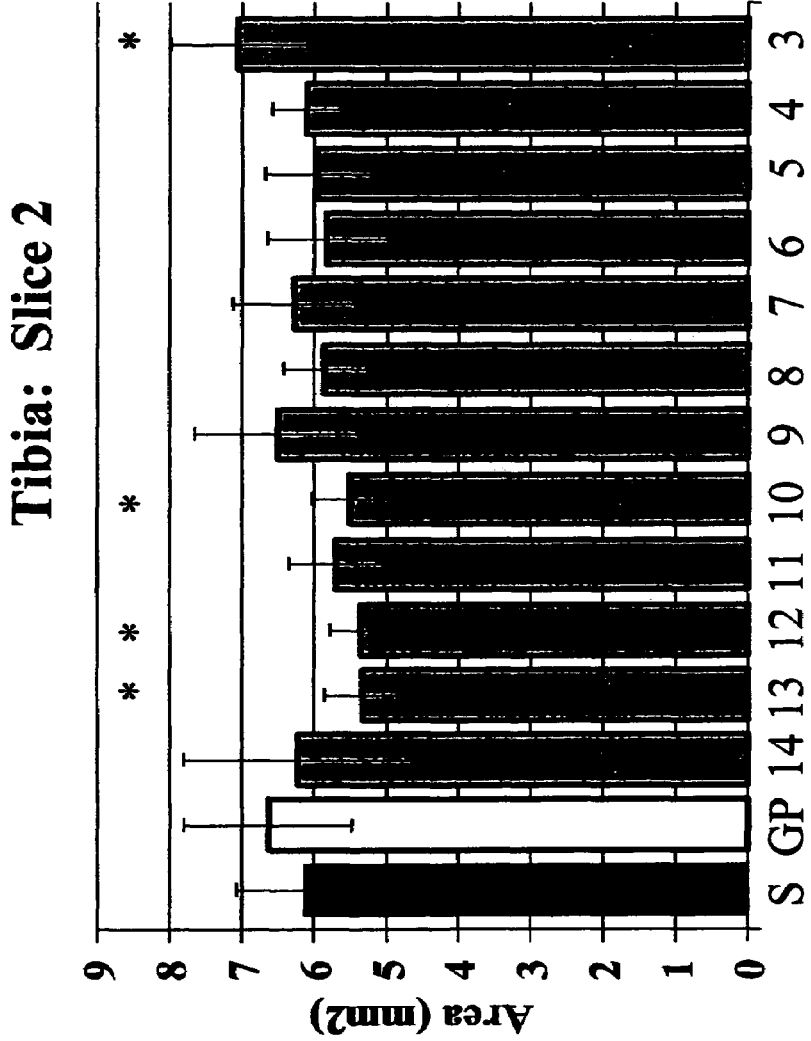
FIG. 14 is a bar graph showing cortical/subcortical area of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.
Figure 15:
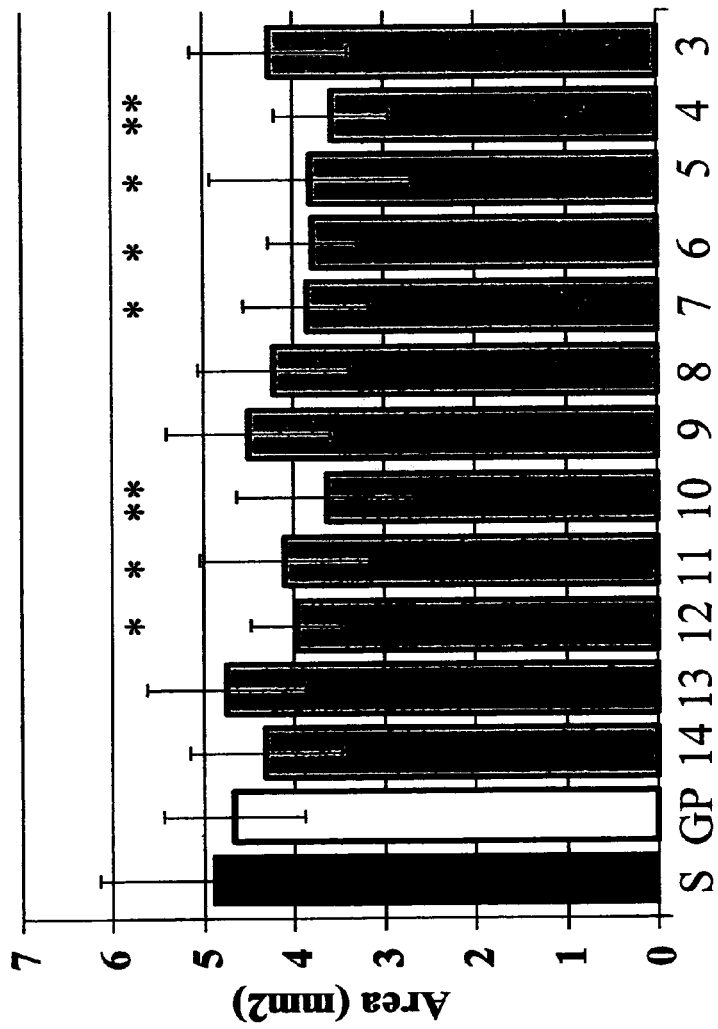
FIG. 15 is a bar graph showing trabecular area of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks
Figure 16:
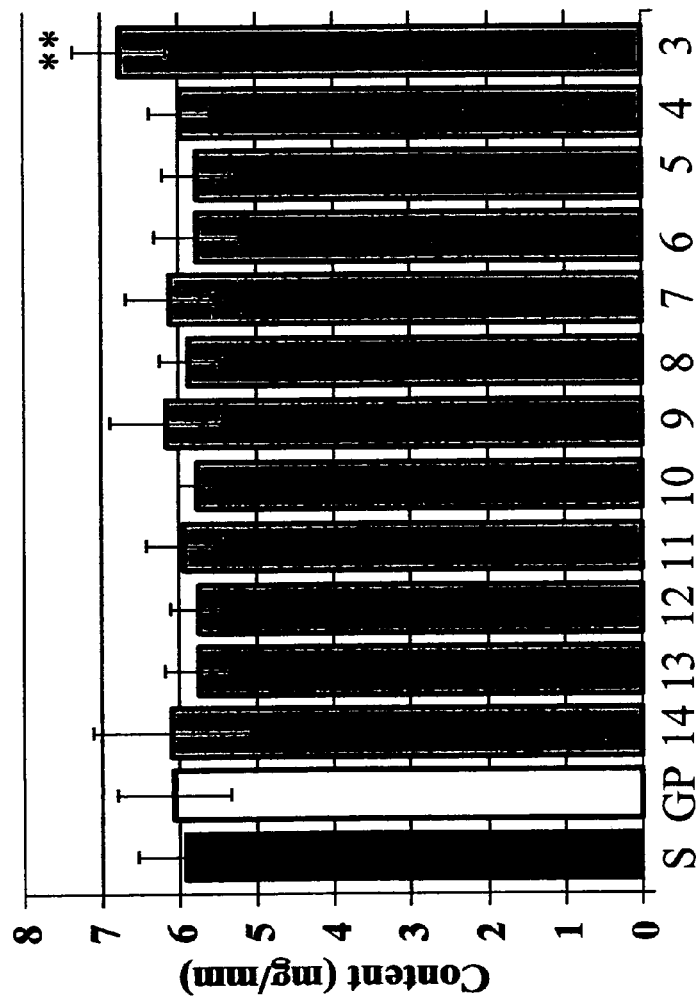
FIG. 16 is a bar graph showing total content of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks
Figure 17:
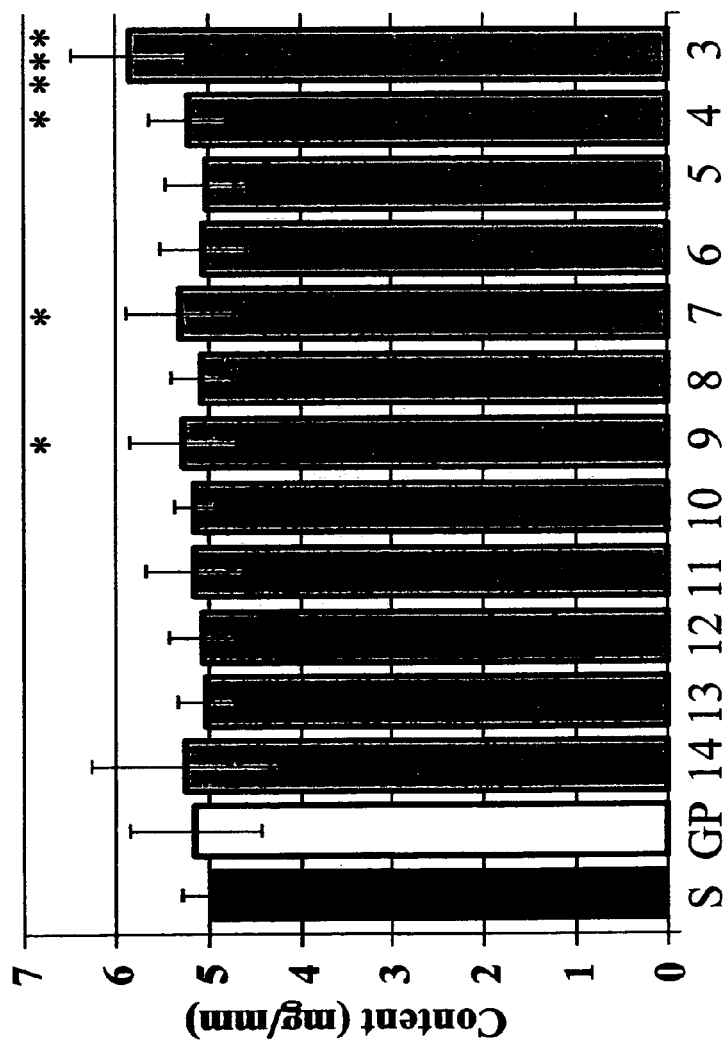
FIG. 17 is a bar graph showing cortical/subcortical content of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.
Figure 18:
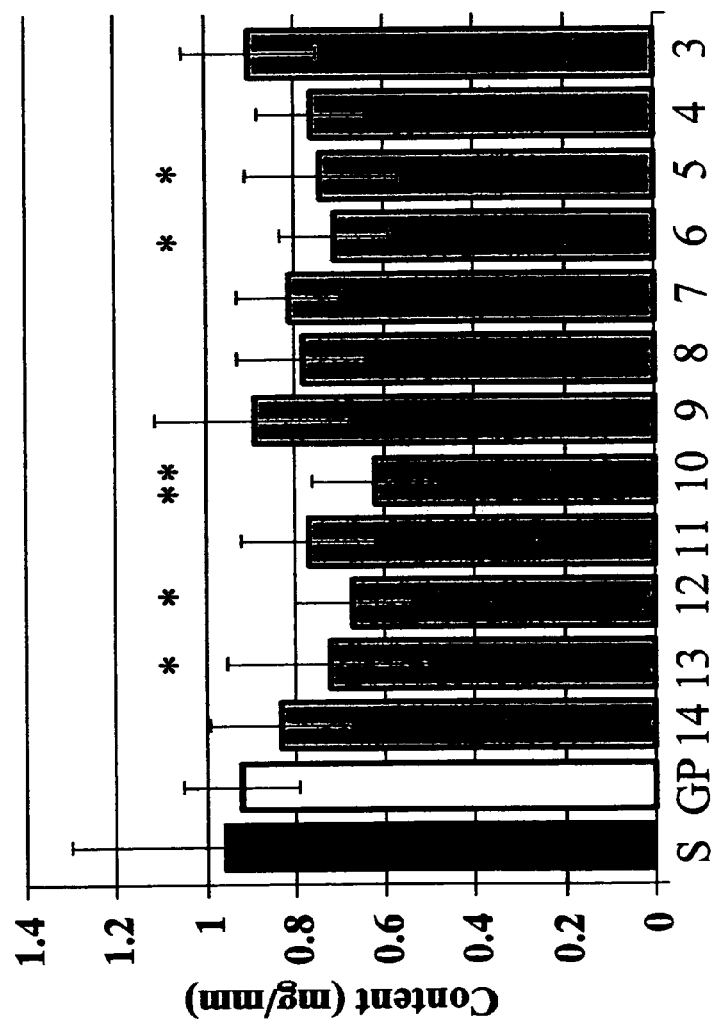
FIG. 18 is a bar graph showing trabecular content of a tibia bone slice from adult animals receiving multiple injections of saline (S), glycosylated fADBP (GP), non-glycyosylated fADBP (14), and non-glycosylated peptides comprising the first 13, 12, 11, 10, 9, 8, 7, 6, 5, 4, and 3 amino acids of SEQ ID NO. 1. Peptide-treated animals received 0.4 ng of the respective peptide/g of body weight every two days for two weeks.

Non-glycosylated DBP peptides of different lengths, at a dosage of 0.4 ng/g of body weight, were administered by subcutaneous injection into normal adult rats every two days for two weeks. The DBP peptides were derived from fADBP and comprised the first 3, 4, 5, 6, 7, 8, 9, 10, 11, 12, and 13 amino acids of SEQ ID NO. 1. After humane sacrifice, the tibia was collected from control and DBP peptide treated rats and analyzed using densitometry techniques with the Norland Medical Systems pQCT scanner. Statistical analysis was performed As shown in FIG. 10, which depicts the results obtained with a representative slice of the tibia, treatment of these animals, which are in the remodeling phase of bone development, the non-glycosylated DBP peptides comprising the first 3, 4, 5, 6, 7, 8, 10, 11, and 12 amino acids of SEQ ID NO. 1 significantly increased total bone density of the tibia. As shown in FIGS. 11 and 12, an increase in cortical/subcortical bone density was the major contributor to the increase in total bone density. In contrast to the results obtained when newborn animals and juvenile animals, which are in a bone growth phase of bone development, treatment of the adult animals with the DBP peptides either had no effect or decreased the cross sectional area of the total cortical and trabecular bone. Similarly, treatment of the adult animals with the DBP peptides either had no effect or decreased the total, cortical, and trabecular content of the bone slice. Measurement of the length of the femurs from the control and peptide-treated animals demonstrated that the present treatment had no effect on bone length.

EXAMPLE 7

Local Administration of Non-Glycosylated fADBP

Young adult rats were injected with 1 μg of non-glycosylated peptide into the distal femur. Control rats were injected with an equal volume of saline. After one week, the animals were sacrificed and the femurs removed for radiologic and histologic analyses.

Figure 19:
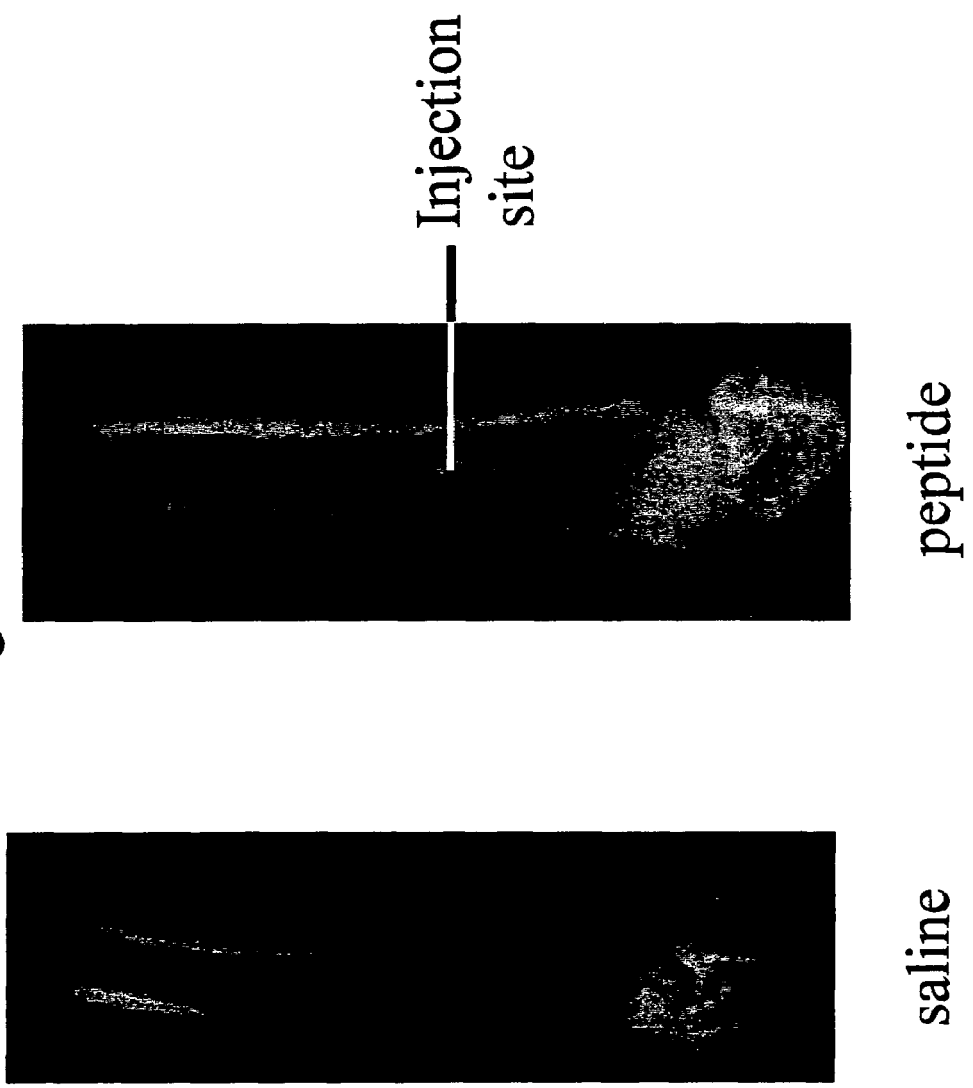
FIG. 19 is an x-ray image demonstrating the effect on bone density of locally administered saline and fADBP. Administration was to the distal femur in young adult rats. The dose was 1 µg of peptide in its non-glycosylated form.

X-rays of the distal femur from treated and control rats are shown in FIG. 19. The graphs show an increase in bone density at the site of injection in the peptide treated rat. Furthermore, the thickness of the cortical bone appears to be increased in the treated animal, and the trabecular bone in the distal metaphysis is also increased in density, both relative to the saline treated animal.

Figure 20:
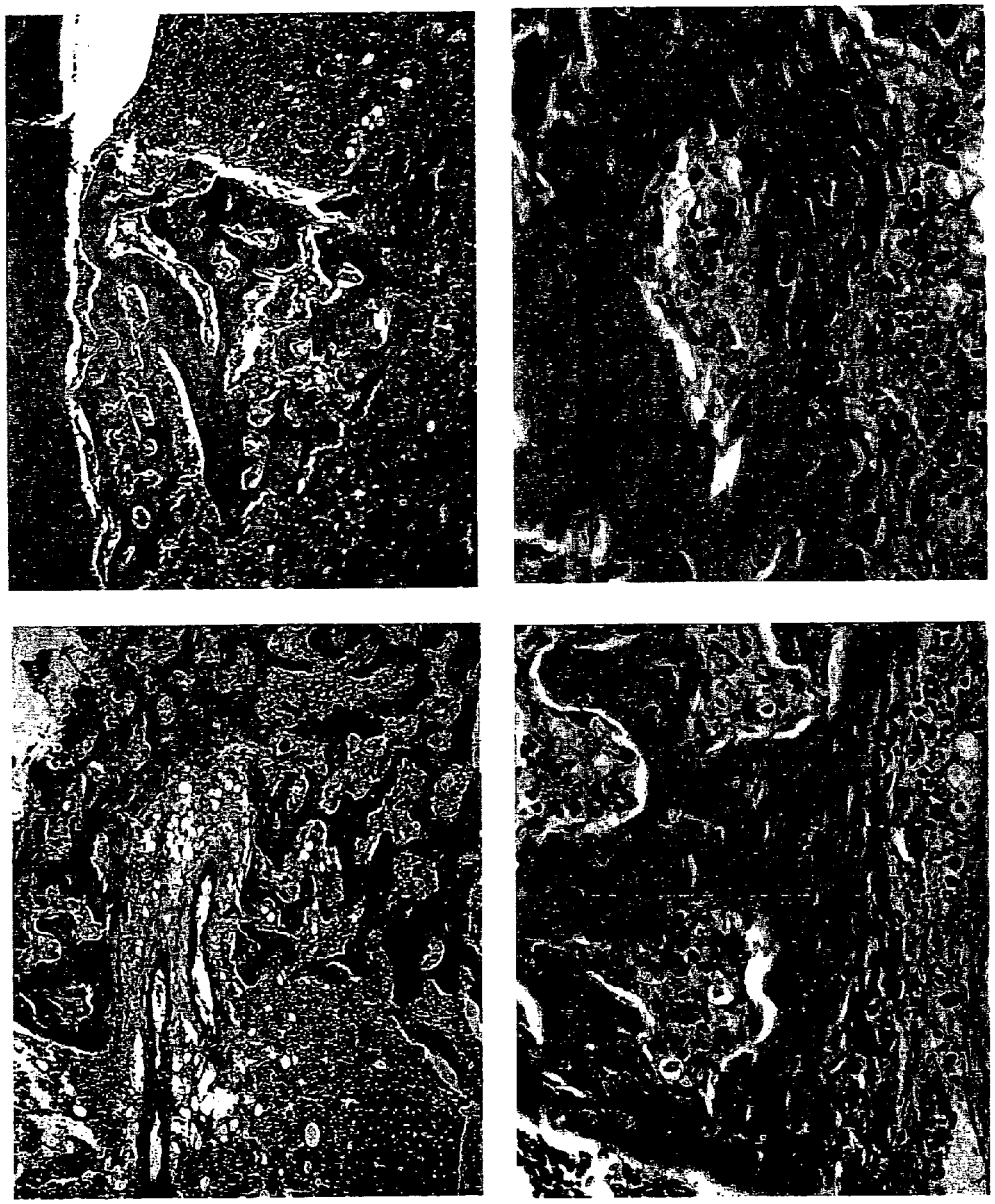
FIG. 20 is a graphical depiction of histological analysis of rat femur after local administration of 1 µg fADBP peptide in its non-glycosylated form. The histological technique is hemotoxylin and eosin (H&E) staining.
Figure 21:
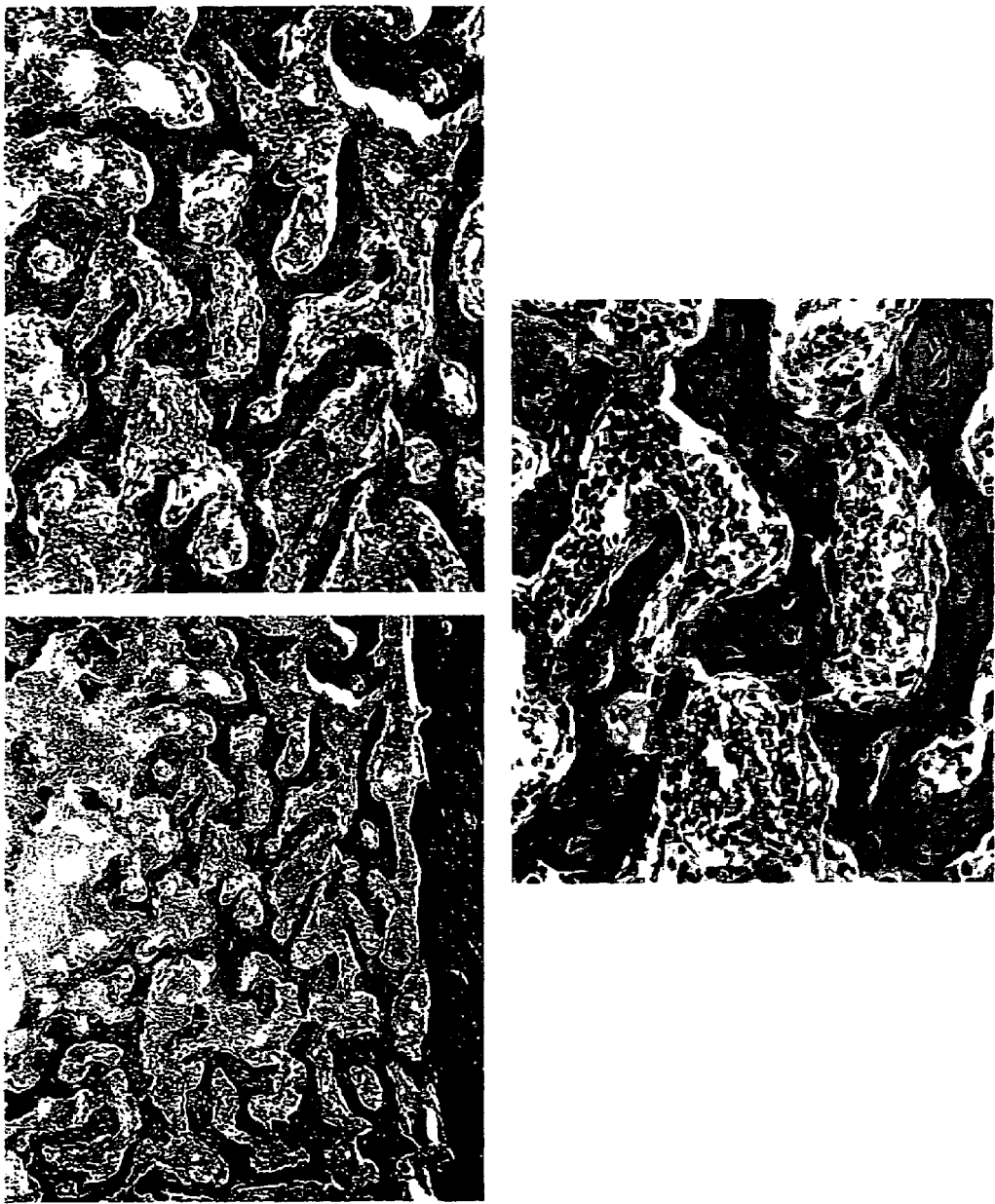
FIG. 21 is a graphical depiction of histological analysis of rat femur after local administration of 1 µg fADBP peptide in its non-glycosylated form. The histological technique is trichrome staining.

Histologic analyses were conducted on sections of femur harvested from the treated and control rats. The histological sections were stained with either H&E or a trichrome stain, and sample slides are shown in FIGS. 20 and 21, respectively. In both analyses, the data show that treatment with peptide results in extensive woven bone at the site of injection. Both FIGS. 20 and 21 depict three different magnifications of 200× (upper left hand part of the figure), 300× (upper right hand part of the figure) and 800× (lower part of the figure). In each case, the woven bone appears histologically normal. The control animals (data not shown) have no new bone at the site of saline injection. It is noted here that bone marrow cells typically occupy the site of injection, and this site would not normally be expected to exhibit bone growth, suggesting the peptide fragments have an osteoinductive action as well as an osteogenic action at the site.

What is claimed is:

1. An isolated peptide for increasing bone density in a mammalian subject, wherein said peptide is glycosylated or lacks a sugar moiety and wherein said peptide is selected from a peptide that is 4 amino acids in length and wherein the amino acid sequence consists of a sequence that is identical to the first 4 consecutive amino acids of SEQ ID NO. 1, a peptide that is 5 amino acids in length and wherein the amino acid sequence consists of a sequence that is identical to the first 5 consecutive amino acids of SEQ ID NO. 1, a peptide that is 6 amino acids in length and wherein the amino acid sequence consists of a sequence that is identical to the first 6 consecutive amino acids of SEQ ID NO. 1, a peptide that is 7 amino acids in length and wherein the amino acid sequence consists of a sequence that is identical to the first 7 consecutive amino acids of SEQ ID NO. 1, a peptide that is 8 amino acids in length and wherein the amino acid sequence consists of a sequence that is identical to the first 8 consecutive amino acids of SEQ ID NO. 1, a peptide that is 10 amino acids in length and wherein the amino acid sequence consists of a sequence that is identical to the first 10 consecutive amino acids of SEQ ID NO. 1, a peptide that is 11 amino acids in length and wherein the amino acid sequence consists of a sequence that is identical to the first 11 consecutive amino acids of SEQ ID NO. 1, a peptide that is 12 amino acids in length and wherein the amino acid sequence consists of a sequence that is identical to the first 12 consecutive amino acids of SEQ ID NO. 1, and a peptide that is 14 amino acids in length and wherein the amino acid sequence consists of a sequence that is identical to the amino acid sequence of SEQ ID NO. 1.

2. The peptide of claim 1 wherein the peptide is glycosylated.

3. The peptide of claim 2, wherein the peptide comprises an N-acetylglucosamine attached to the threonine at the amino terminus of the peptide.

4. The peptide of claim 1, wherein the peptide lacks a sugar moiety.

5. The peptide of claim 1, wherein the peptide is 10 amino acids in length and wherein the amino acid sequence consists of a sequence that is identical to the first 10 consecutive amino acids of SEQ ID NO. 1.

6. The peptide of claim 1, wherein the peptide is four amino acids in length and wherein the amino acid sequence consists of a sequence that is identical to the first 4 consecutive amino acids of SEQ ID NO. 1.

7. The peptide of claim 1, wherein the peptide is 12 amino acids in length and wherein the amino acid sequence consists of a sequence that is identical to the first 12 consecutive amino acids of SEQ ID NO.1.

8. The peptide of claim 1, wherein the peptide is 11 amino acids in length and wherein the amino acid sequence consists of a sequence that is identical to the first 11 consecutive amino acids of SEQ ID NO. 1.

9. The peptide of claim 1, wherein the peptide is 14 amino acids in length and wherein the amino acid sequence consists of a sequence that is identical to the sequence of SEQ ID NO: 1.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Homo sapiens

<400> SEQUENCE: 1

Thr Pro Thr Glu Leu Ala Lys Leu Val Asn Lys Arg Ser Glu
1               5                   10